(12) United States Patent
Rothweiler et al.

(10) Patent No.: US 7,615,002 B2
(45) Date of Patent: Nov. 10, 2009

(54) ENDOSCOPE

(75) Inventors: Christoph Rothweiler, Donaueschingen (DE); Andreas Grossmann, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 864 days.

(21) Appl. No.: 10/886,058

(22) Filed: Jul. 6, 2004

(65) Prior Publication Data

US 2005/0021010 A1    Jan. 27, 2005

Related U.S. Application Data

(63) Continuation of application No. PCT/EP03/12634, filed on Nov. 12, 2003.

(30) Foreign Application Priority Data

Nov. 20, 2002  (DE)  ............................... 102 55 082

(51) Int. Cl.
*A61B 1/00* (2006.01)
(52) U.S. Cl. .................. 600/104; 600/114; 600/129
(58) Field of Classification Search ......... 600/104–106, 600/114, 137, 156, 125, 136, 172, 121, 127, 600/129, 130, 174, 175
See application file for complete search history.

(56) References Cited

U.S. PATENT DOCUMENTS

| | | | | |
|---|---|---|---|---|
| 3,889,662 A | * | 6/1975 | Mitsui | ......................... 600/139 |
| 4,430,996 A | * | 2/1984 | Bonnet | ........................ 600/105 |
| 4,702,229 A | | 10/1987 | Zobel | |
| 4,765,314 A | | 8/1988 | Kolditz et al. | |
| 4,784,117 A | * | 11/1988 | Miyazaki | ..................... 600/114 |
| 5,287,845 A | * | 2/1994 | Faul et al. | .................... 600/135 |
| 5,349,942 A | | 9/1994 | Heimberger | |
| 5,486,155 A | * | 1/1996 | Muller et al. | ................ 600/137 |
| 5,582,575 A | | 12/1996 | Heckele et al. | |
| 5,607,435 A | * | 3/1997 | Sachdeva et al. | ............. 606/139 |
| 5,733,242 A | * | 3/1998 | Rayburn et al. | .............. 600/120 |

(Continued)

FOREIGN PATENT DOCUMENTS

DE          35 12 602          10/1986

(Continued)

OTHER PUBLICATIONS

Excerpt of catalogue of Karl Storz GmbH & Co., "Die Welt Der Endoskopie Plastische Chirurgie," Jan. 1999, $2^{nd}$ Edition, Optiken und Instrumente, "Hopkins II Optiken" and "Optische Retraktoren" (5 pages).

(Continued)

*Primary Examiner*—John P Leubecker
*Assistant Examiner*—Victoria W Chen
(74) *Attorney, Agent, or Firm*—Lipsitz & McAllister, LLC (57) ABSTRACT

In an endoscope having a proximal end area, a distal end area introducible into the body of a human being, a shaft extending in a longitudinal direction, and an optical device extending through the shaft in the longitudinal direction thereof and movable relative to the shaft, to enable particularly easy and safe handling of the optical device it is proposed that the optical device be fixable in axial direction relative to the shaft in a first position and in at least a second position differing from the first position.

27 Claims, 5 Drawing Sheets

U.S. PATENT DOCUMENTS

| | | | |
|---|---|---|---|
| 5,807,240 A * | 9/1998 | Muller et al. | 600/135 |
| 5,843,000 A * | 12/1998 | Nishioka et al. | 600/104 |
| 5,954,632 A | 9/1999 | Heckele et al. | |
| 6,099,550 A * | 8/2000 | Yoon | 606/205 |
| 6,129,683 A | 10/2000 | Sutton et al. | |
| 6,264,664 B1 * | 7/2001 | Avellanet | 606/128 |
| 6,350,234 B1 | 2/2002 | Foerster-Klein et al. | |
| 6,358,200 B1 * | 3/2002 | Grossi | 600/156 |
| 6,419,626 B1 * | 7/2002 | Yoon | 600/109 |
| 6,436,117 B1 | 8/2002 | Waller et al. | |
| 6,464,631 B1 * | 10/2002 | Girke et al. | 600/109 |
| 6,471,639 B2 | 10/2002 | Rudischhauser et al. | |
| 6,695,772 B1 * | 2/2004 | Bon et al. | 600/114 |
| 6,743,166 B2 | 6/2004 | Berci et al. | |
| 6,808,491 B2 * | 10/2004 | Kortenbach et al. | 600/104 |
| 7,070,602 B2 * | 7/2006 | Smith et al. | 606/143 |
| 2001/0053873 A1 * | 12/2001 | Schaaf et al. | 600/104 |
| 2001/0056222 A1 | 12/2001 | Rudischhauser et al. | |
| 2002/0049367 A1 * | 4/2002 | Irion et al. | 600/173 |
| 2002/0072652 A1 | 6/2002 | Berci et al. | |
| 2002/0183589 A1 * | 12/2002 | Brommersma et al. | 600/105 |
| 2003/0144661 A1 * | 7/2003 | Brommersma et al. | 606/46 |
| 2004/0019256 A1 * | 1/2004 | Cubb et al. | 600/188 |

FOREIGN PATENT DOCUMENTS

| | | |
|---|---|---|
| DE | 39 20 706 | 1/1991 |
| DE | 42 18 706 | 12/1993 |
| DE | 44 05 720 | 10/1995 |
| DE | 197 21 138 | 9/1998 |
| DE | 198 13 781 | 10/1999 |
| DE | 198 22 167 | 12/1999 |
| DE | 200 03 797 | 8/2000 |
| DE | 201 12 949 | 12/2001 |
| WO | 00/48505 | 8/2000 |

OTHER PUBLICATIONS

Excerpt of catalogue of Karl Storz GmbH & Co., "The World of Endoscopy Aesthetic Surgery," Jan. 1999, $2^{nd}$ Edition Telescopes and Instruments, "Hopkins II Telescopes" and "Optical Retractors"(5 pages).

Photographic representations of Karl Storz Endoscopy Instruments—Figures 1-9 (undated).

Karl Storz—Endoskope Engineering Drawings, Nos. 50200R (Jun. 27, 1996); 6821991 (Jul. 23, 1997); 7987890 (Jun. 28, 1996); 7685290 (Jul. 11, 1994) and 7684990 (Jul. 11, 1994).

* cited by examiner

ENDOSCOPE

This application is a continuation of international application number PCT/EP03/12634 filed on Nov. 12, 2003.

The present disclosure relates to the subject matter disclosed in international application PCT/EP03/12634 of Nov. 12, 2003, which is incorporated herein by reference in its entirety and for all purposes.

BACKGROUND OF THE INVENTION

The invention relates to an endoscope having a proximal end area, a distal end area introducible into the body of a human being, a shaft extending in a longitudinal direction, and an optical device extending through the shaft in the longitudinal direction thereof and movable relative to the shaft.

Endoscopes of the kind described hereinabove are used for various purposes when performing minor surgery on the human body. An operating surgeon can view the operating site with the aid of the optical device extending through the shaft. With conventional endoscopes, the optical device is introducible from the proximal end into the shaft and displaceable therein in axial direction. It has proven to be disadvantageous that the optical device can be moved in an uncontrolled manner.

The object of the present invention is, therefore, to so improve an endoscope of the kind mentioned hereinabove that the optical device is easier and safer to handle.

SUMMARY OF THE INVENTION

This object is accomplished with a generic endoscope, in accordance with the invention, in that the optical device is fixable in axial direction relative to the shaft in a first position and in at least a second position differing from the first position.

This configuration makes it possible for the optical device to be held in precisely defined positions at least in the longitudinal direction of the shaft. An undesired relative movement between the shaft and the optical device is thereby avoided. By selecting two positions, for example, a diagnosis position and a work position, the optical device can be employed in the desired manner. Thus, for example, in the diagnosis position, it can protrude far beyond the distal end of the endoscope without the distal end of the endoscope or tools arranged thereon impeding a view of the operating site. By transferring the optical device from the diagnosis position to the second position serving, for example, as work position, an optical monitoring of employment of tools arranged on the shaft is rendered possible in a defined manner. In the second position, a free end of the optical device could, however, also be retracted into the shaft to such an extent that the optical device is protected. Owing to the possibility of axially fixing the optical device in two positions relative to the shaft, considerably easier and safer handling of the endoscope is possible.

The optical device is fixable in axial direction in a particularly simple way when at least one locking device is provided for fixing the optical device in the first position and/or the second position. In particular, the optical device can thereby be fixed automatically upon reaching one of the two predetermined positions. With corresponding design of the locking device, the fixed optical device can also be released again and moved in axial direction.

The optical device is preferably fixed in circumferential direction relative to the shaft in the first position and/or in the second position. This results in a fully defined position of the optical device relative to the shaft.

It is expedient for the optical device to be fixable in axial direction and to be freely rotatable about the longitudinal axis of the shaft in a third position. In the third position, the optical device may, for example, be completely retracted into the interior of the shaft, which protects it against outer influences. A free rotatability about the longitudinal axis of the shaft makes it possible for connection lines proceeding from the proximal end of the optical device to be orientated in any chosen way.

Provision may be made in a preferred embodiment of the invention for the distal end of the optical device to protrude in the first position over the distal end of the endoscope. An operating site which can be viewed by the optical device is thus not restricted by the endoscope or elements arranged thereon.

In the second position, it is expedient for the distal end of the optical device to project over the distal end of the shaft, and for the distal end of the endoscope to project over the optical device. When the second position is provided in such a way, the distal end of the endoscope which is formed, for example, by tool elements projecting from the shaft can be viewed with the optical device. A movement of tool elements during use is thus optically controllable.

To enable use of conventional optical devices in conjunction with an endoscope according to the invention, provision may be made for the endoscope to comprise a device for receiving the optical device, for the device for receiving the optical device to be movable relative to the shaft and fixable in axial direction in the first position and/or in the second position and/or in the third position. The at least one position in which the optical device is fixable in axial direction relative to the shaft is now defined by a corresponding configuration of the endoscope and the device for receiving the optical device.

The optical device is preferably freely rotatable about the longitudinal axis relative to the device for receiving the optical device. In this way, the optical device can be freely rotated and an operating site freely viewed even when the device for receiving the optical device is fixed in axial direction. Furthermore, connection lines proceeding from a proximal end of the optical device can be orientated in any desired way.

A particularly simple design of the locking device is obtained when the locking device comprises a locking member movable relative to a locking recess, when the locking recess or the locking member is arranged on the optical device or on the device for receiving the optical device, and when the locking member or the locking recess is arranged on a receptacle of the endoscope for the optical device or the device for receiving the optical device. A fixing of the respective position is achieved by the locking member dipping into the locking recess. Conversely, release is achievable in a simple way by the locking member being guided out of the locking recess.

Provision may be made in accordance with a further preferred embodiment of the invention for the endoscope to comprise an inflow channel for feeding a fluid from the proximal to the distal end area, an outflow channel for conducting a fluid away from the distal to the proximal end area, an inflow connection in flow communication with the inflow channel, and an outflow connection in flow communication with the outflow channel. Owing to this configuration, a fluid can be conducted via the inflow connection from the proximal end to the distal end of the endoscope and issue there, for example, to flush the operating site. At the same time, the fluid or body tissue which has been removed can be conducted away through the outflow channel.

It is expedient for the inflow connection, the outflow connection and the optical device to be rotatable relative to one another about an axis of rotation extending substantially in the longitudinal direction of the shaft. In this way, connection lines proceeding from the respective connections can be arranged in any chosen position, which also reduces the danger of the connection lines becoming twisted or knotted together.

Furthermore, it is advantageous for the inflow connection, the outflow connection and the optical device to be rotatable relative to the shaft about the axis of rotation extending substantially in longitudinal direction of the shaft. Owing to this configuration, the shaft can be introduced into the interior of the body and left lying there in a non-rotatable manner. On the other hand, lines proceeding from the inflow connection, the outflow connection or the optical device can be orientated in any chosen way so as not to obstruct the operator or so as to prevent twisting of the lines. Furthermore, owing to the shaft resting in this way within the body, the risk of damage to the interior of the body owing to rotation of the shaft is virtually excluded.

In order not only to be able to view an operating site with the endoscope but also to be able to actually perform surgery, it is expedient for at least one movable tool to be arranged at the distal end of the shaft. The tool may be, for example, a fixation forceps, scissors or the like.

It is advantageous for the movable tool to be rotatable relative to the shaft about an axis of rotation extending substantially in the longitudinal direction of the shaft. A relative position of the movable tool relative to a shaft which is stationary within the body can thus be optionally altered.

Provision may be made in a preferred embodiment of the invention for the tool to comprise at least one jaw part which is mounted for movement relative to the shaft. Scissors or fixation forceps can thus be formed in a simple way.

To increase a range of action of the tool, it is expedient for at least two jaw parts which are movable relative to each other to be provided. These may, for example, be pivoted outwardly far beyond a cross-sectional area of the shaft and grasp body tissue, in particular, for the removal of septa, polyps or the like, some of which are of larger cross section than the cross section of the shaft introduced into the interior of the body.

It is advantageous for the at least one movable jaw part to be pivotable relative to the shaft about a pivot axis extending substantially transversely to the longitudinal direction of the shaft. A pivotal movement of the jaw part, in particular, a sideways pivoting of the jaw part, can thereby be implemented in a particularly easy way.

It is preferable for an actuating device associated with the at least one jaw part to be provided and for the actuating device to be rotatable relative to the shaft. A movement of the jaw part can be brought about with the actuating device. Owing to the rotatability of the actuating device relative to the shaft, a conclusion can be drawn from the position of the actuating device as to the relative orientation of the associated jaw part.

For example, in order to keep a fixation forceps in a closed position, it is expedient for the actuating device to be lockable in an actuated position of the at least one movable jaw part. Locking is, however, also conceivable in an open position of the jaw parts.

It is expedient for at least two jaw parts to be provided, which, in a closed position in which the two jaw parts rest against each other, are formed symmetrically in relation to a plane containing the longitudinal axis of the shaft. Irrespective of whether only one or both of the jaw parts are movably mounted on the shaft, a particularly simple design of the endoscope is thereby achieved.

Preferably, the optical device is arranged in the area of the at least two jaw parts on a side of the stationary jaw part, and the movable jaw part is arranged on that side of the stationary jaw part which faces away from the optical device. The optical device is thus arranged outside the work area of the two jaw parts and cannot get in between these and thereby become damaged. Rather, in this way it is arranged so as to be protected.

A particularly good protection of the optical device is obtained when the stationary jaw part is concavely curved in the direction pointing towards the optical device. The optical device can thus lie snugly against the concave area of the jaw part. The cross section of the portion of the endoscope introducible into the interior of the body is thereby also minimized.

Provision may be made in accordance with a further preferred embodiment of the invention for the shaft to have adjacent to the distal end of the endoscope a shaft section which is introducible into the body of a human being, for the axis of symmetry of the optical device in the area of the shaft section to extend parallel to the axis of symmetry of the shaft in the area of the shaft section, and for both axes of symmetry to be spaced from each other. Such an eccentric arrangement of the longitudinal axes of the shaft section and the optical device make it possible for the shaft and, in particular, tools arranged thereon to be rotatable about the optical device. The longitudinal axis of the optical device thus also forms, as a whole, the axis of rotation for the entire portion of the endoscope that is introducible into the interior of a body.

For use of the endoscope in the field of high-frequency surgery, it is advantageous for an HF connecting device to be provided for connecting the endoscope to a high-frequency generator and for this HF connecting device to be arranged so as to be rotatable relative to the optical device. Connection lines can thus also be arranged in any desired orientation, and twisting of the connection lines is thereby prevented.

The following description of a preferred embodiment of the invention serves in conjunction with the drawings to explain the invention in further detail.

DETAILED DESCRIPTION OF THE INVENTION

Figure 1:
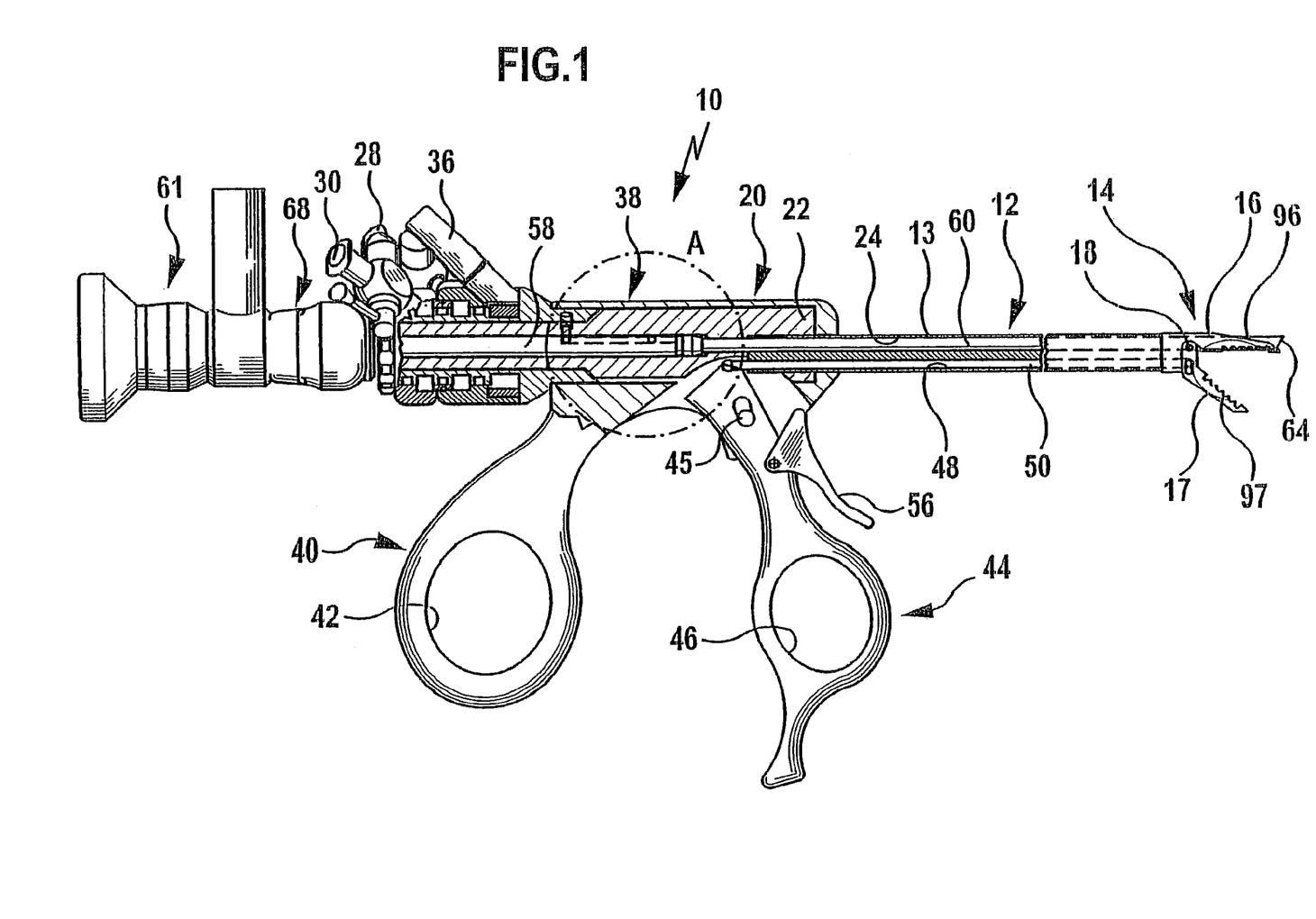
FIG. 1 is a partly sectional side view of an endoscope.

FIG. 1 shows an endoscope generally designated by reference numeral 10 with a shaft 12 for introduction into the interior of the body of a human being through an opening of the body. A surgical tool in the form of a fixation forceps 14 is arranged at the distal end of the shaft 12 for rotation about the longitudinal axis of the shaft 12 relative thereto. The fixation forceps comprises a stationary jaw part 16 and a jaw part 17 which is mounted for pivotal movement about a pivot axis 18 extending transversely to the longitudinal axis of the shaft 12.

Adjoining a proximal end of the shaft 12 is a handling portion 20 of the endoscope 10, which comprises a main body 22 rigidly connected to an outer shaft sleeve 13 of the shaft 12. Extending through the shaft 12 and the main body 22 is an optical channel 24 which widens in the form of a step in the area of the main body 22 in the direction towards its proximal end, thereby forming a ring-shaped stop 26. Provided in the proximal end area of the main body 22 for rotation around the main body 22 and relative to each other are an inflow connection 28 and an outflow connection 30, which are in flow communication with an inflow channel 32 and an outflow channel 34, respectively, which are of lens-shaped cross-section and extend through the main body 22 and the shaft 12. Also mounted for rotation on the main body 22 is an HF connection 36 which is conductively connected to the two jaw parts 16 and 17 via electric connections, not shown, which extend in the longitudinal direction through the shaft 12.

Arranged for rotation about a distal portion of the main body 22 is a grip portion 38 which comprises a stationary branch 40 projecting sideways from the main body 22 and pointing in proximal direction with a thumb opening 20, and a branch 44 pivotal on the grip portion 38 about a pivot axis 45 extending transversely to the longitudinal axis of shaft 12 relative to the branch 40 with a finger opening 46. Inserted into a manipulation channel 48 extending through the shaft 12 in the longitudinal direction thereof is a push-and-pull rod 50 whose proximal end is movably mounted on the branch 44 and whose distal end is movably connected to the jaw part 17 via bearing pins 54 protruding at the sides and extending into guide slots 52 of the jaw part 17. By a pivotal movement of the branch 44 the push-and-pull rod 50 is moved in the longitudinal direction of the shaft 12, whereby the jaw part 17 is pivoted relative to the jaw part 16.

With the locking lever 56 a pivoted position of the branch 44 relative to the branch 40 can be locked, whereby the movable jaw part 17 is held in a desired position, for example, in abutment against the stationary jaw part 16 or in an open position in which it is turned sideways away from the jaw part 16.

Inserted into the optical channel 24 at the proximal end is a guide sleeve 58 which rests with its distal end almost at the stop 26. The guide sleeve 58 is part of an optical adapter 68 via which a connection portion 61 at the proximal end of an optical device 60 is connectable to further optical devices, for example, a camera, a microscope or the like. By means of a connection between the optical adapter 68 and the connection portion 61, an axial fixing of the two elements is achievable, for example, via a releasable locking connection. A relative axial movement between the guide sleeve 58 and the optical device 60 is thereby prevented in the connected state. If desired, the locking connection may be designed so as to allow rotation of the connection portion 61 relative to the optical adapter 68.

The rod-shaped optical device 60 can be pushed in through the guide sleeve 58 from the proximal end of the endoscope 10. The optical device 60 has an end 64 which is beveled relative to its longitudinal axis 62 and is formed by a surface inclined at an angle of inclination 66 relative to the longitudinal axis 62.

Figure 2:
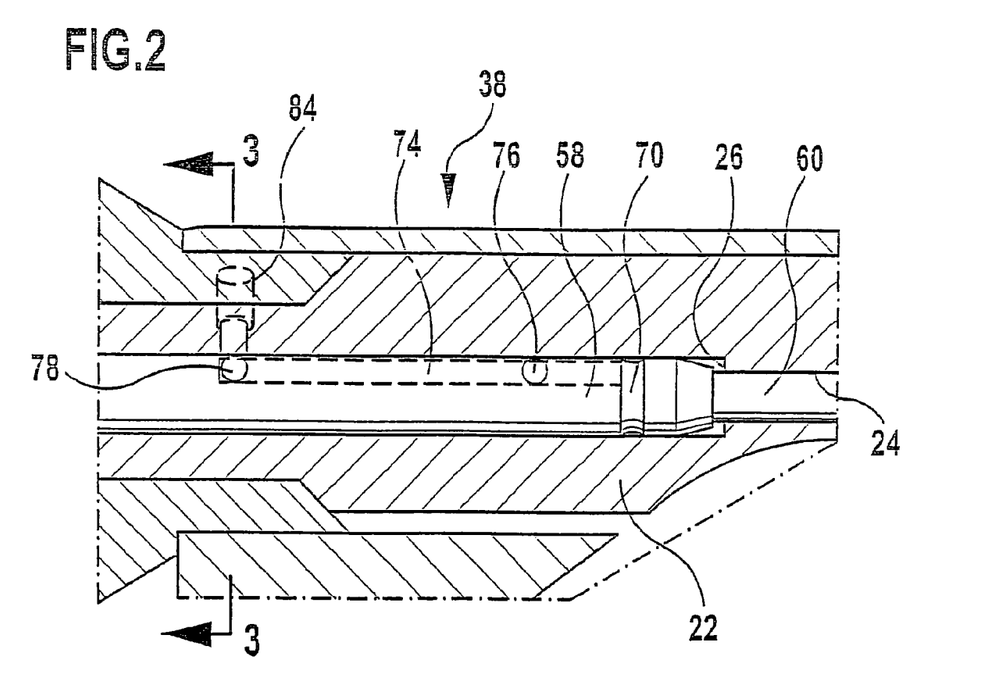
FIG. 2 is an enlarged sectional view of area A in FIG. 1.
Figure 3:
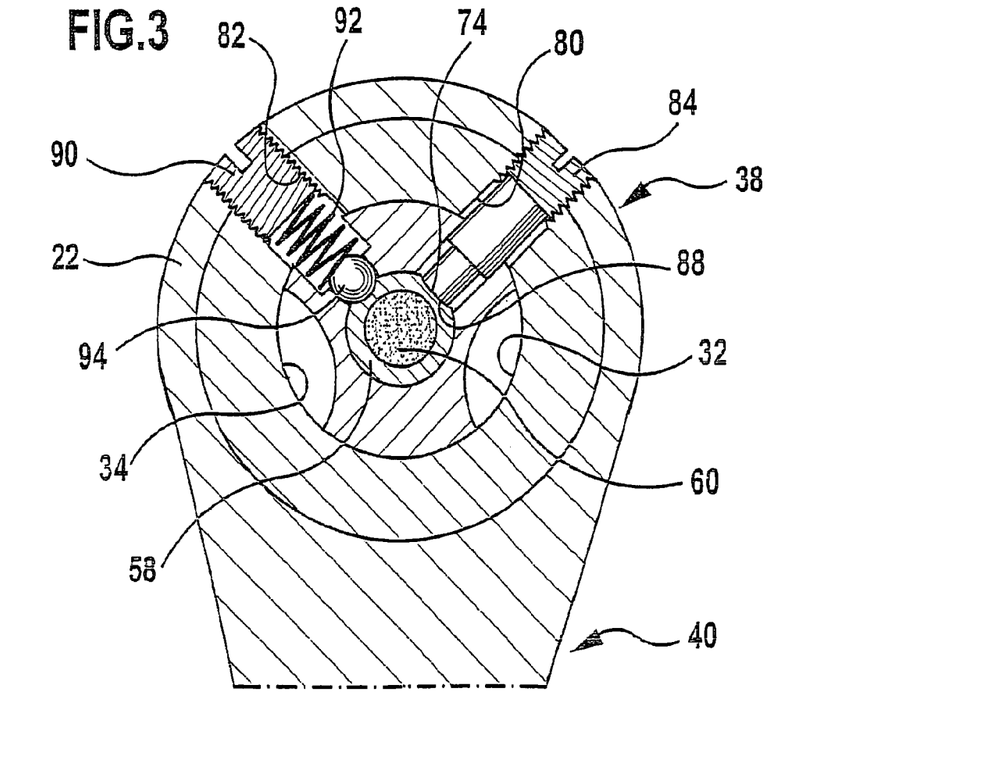
FIG. 3 is a cross-sectional view taken along line 3-3 in FIG. 2.
Figure 4:
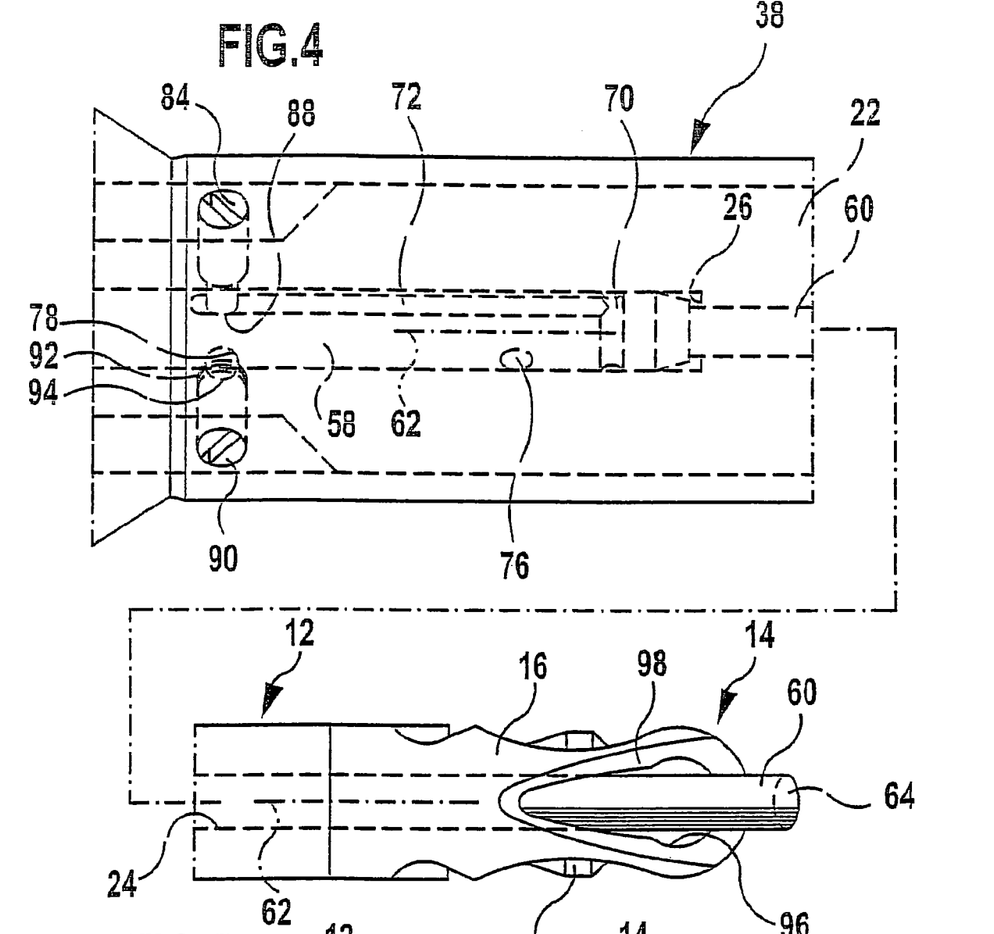
FIG. 4 is a partly broken open plan view of an endoscope with an optical device in a diagnosis position.
Figure 6:
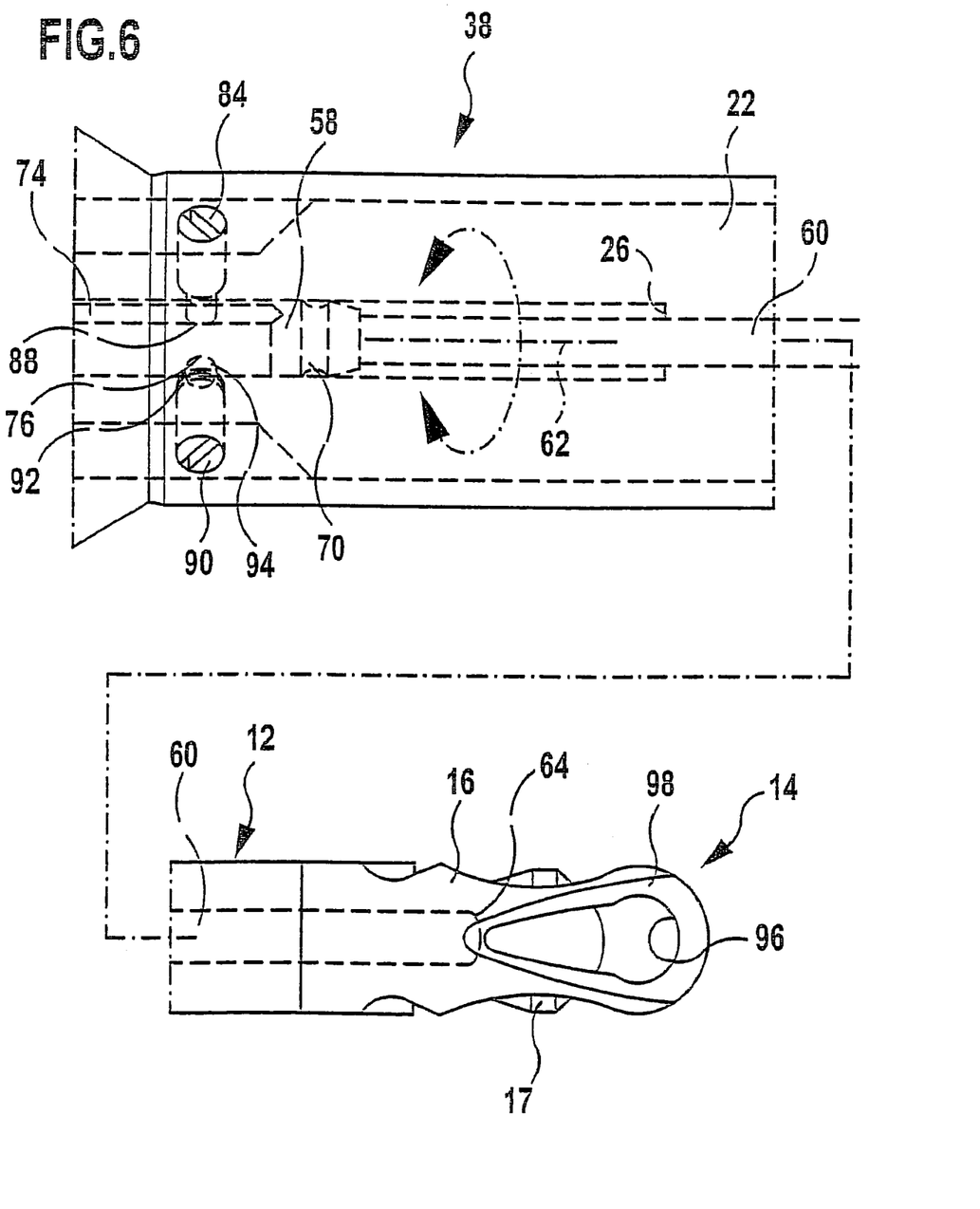
FIG. 6 is a plan view similar to FIG. 4 with the optical device in a work position.

As shown in FIGS. 2, 3 and 6, the guide sleeve 58 has adjacent to its distal end an annular groove 70, from which there extends in proximal direction along its outer surface over approximately half of the length of the guide sleeve 58 a flattened portion 74. Alternatively, as shown in FIG. 4, a longitudinal groove 72 may be provided instead of the flattened portion 74. On the guide sleeve 58 two hollow sphere-type recesses 76 and 78 are spaced from each other in the longitudinal direction and offset through 90° in the circumferential direction. The spacing between recess 76 and recess 78 corresponds approximately to the length of the movable jaw part 17. The spacing between the recess 76 and the annular groove 70, on the other hand, is significantly smaller.

The grip portion 38 is provided with two radial threaded bores 80 and 82 offset in relation to each other through approximately 90° in circumferential direction for guiding the guide sleeve 58. Inserted into the threaded bore 80 is a threaded pin 84 whose end 88 is designed so as to correspond to the longitudinal groove 72 as shown, for example, in FIG. 4 or whose flattened end 88 corresponds to the flattened portion 74 as shown, in particular, in FIG. 3. Inserted into the threaded bore 82 is a headless screw 90 on which a helical spring 92 is supported in the direction towards the guide sleeve 58 and presses a ball 94 against the guide sleeve 58. In combination the headless screw 90, the helical spring 92 and the ball 94 form a ball thrust member via which a locking connection can be made with the two recesses 76 and 78 provided on the guide sleeve 58 and forming locking recesses. The threaded pin 84 is screwed into the threaded bore 80 until the end 88 dips into the longitudinal groove 72 and the guide sleeve 58 is thereby guided in the longitudinal direction thereof. The guide sleeve 58 is fixed in axial direction relative to the grip portion 38 and hence to the shaft 12 when the ball 94 dips into one of the two recesses 76 or 78 or into the annular groove 70. In the last mentioned case, rotation of the grip portion 38 about the optical adapter 68 is possible.

Owing to the configuration of the two recesses 76 and 78 and of the annular groove 70, the optical adapter 68 is fixable in three axial positions relative to the shaft 12, which will be explained in further detail in conjunction with FIGS. 4 to 7.

Figure 5:
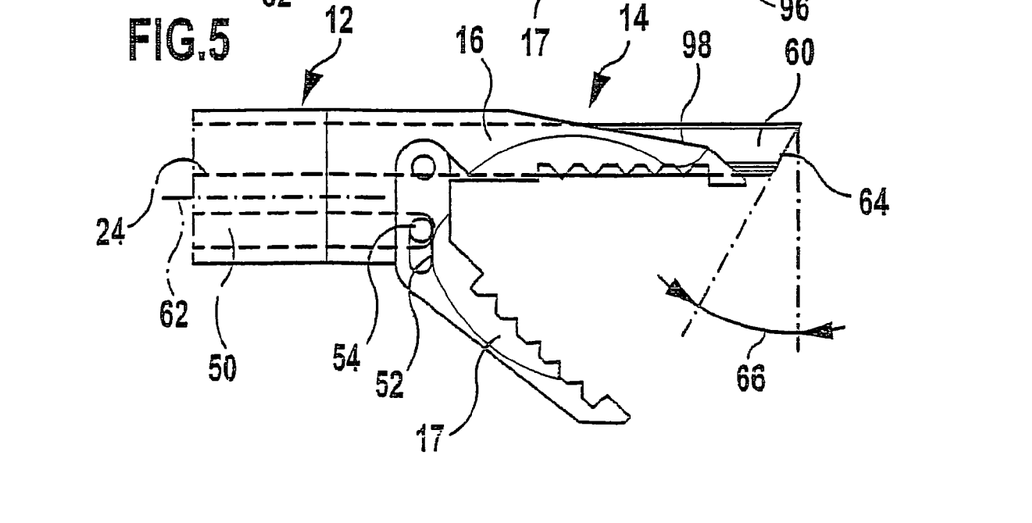
FIG. 5 is a side view of the end portion of the endoscope shown in FIG. 4.

In the so-called diagnosis position the ball 94 dips into the recess 78. The end 64 of the optical device 60 protrudes in the diagnosis position somewhat beyond the end of the stationary jaw part 16 in the distal direction. In this way, an operating site can be viewed without the two jaw parts 16 and 17 impeding the view. This is shown in FIGS. 4 and 5. In the work position shown in FIG. 6 the ball 94 dips into the recess 76. In this position the end 64 of the optical device 60 protrudes somewhat over the optical channel 24 out of the shaft 12, but not beyond the distal end of the fixed jaw part 16. In this work position, surgery performed with the jaw parts 16 and 17 can be observed with the optical device 60.

Figure 7:
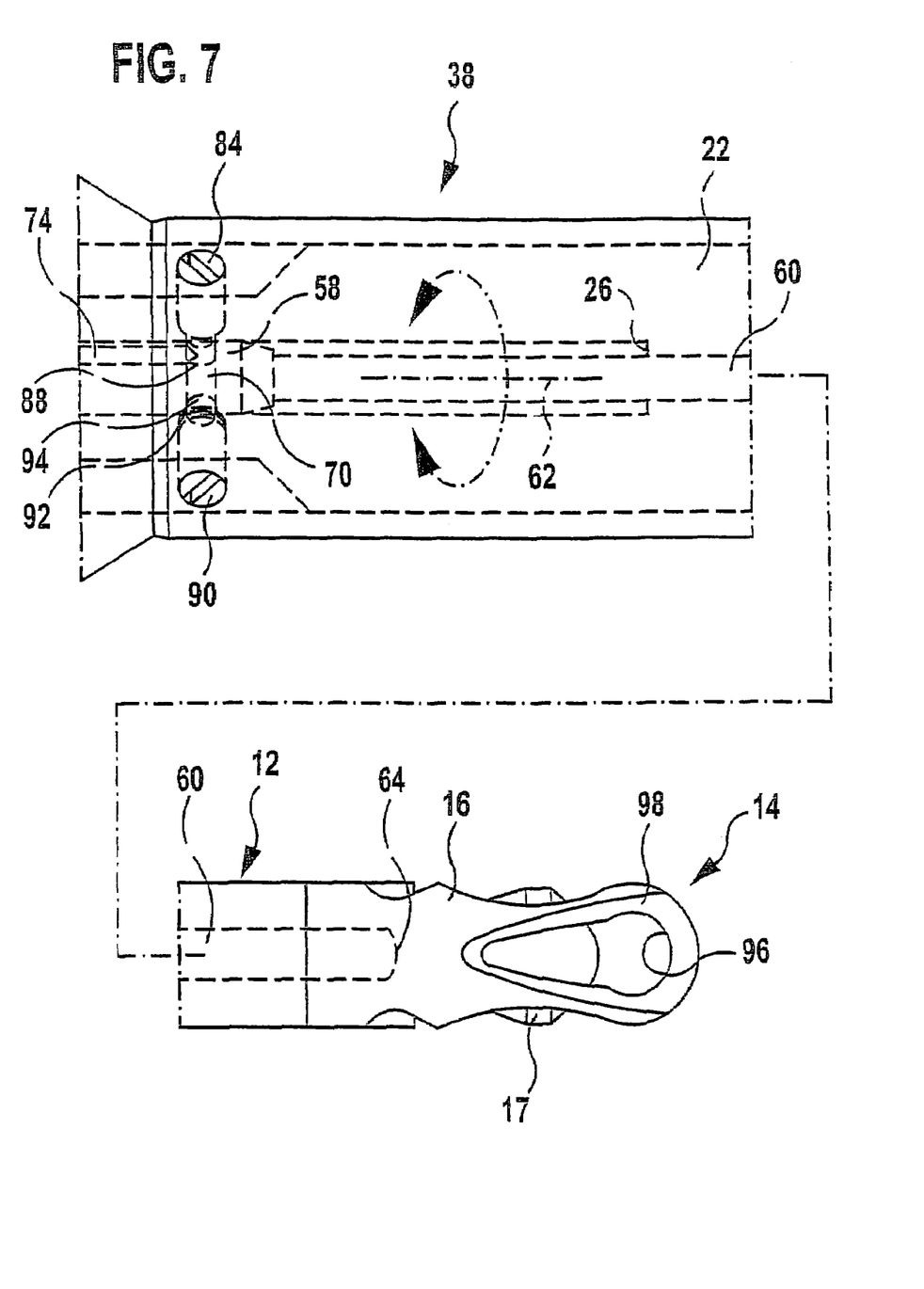
FIG. 7 is a plan view similar to FIG. 4 with the optical device in a retracted position.

When the optical adapter 68 is retracted even further in axial direction, the ball 94 finally dips into the annular groove 70 into which the free end 88 of the threaded pin 84 also dips simultaneously, and rotation of the guide sleeve 58 relative to the grip portion 38 is thereby enabled. In this third position of the optical adapter 68, the end 64 of the optical device 60 is retracted into the optical channel 24 so that the end 64 is protected.

In the area of the shaft 12, the longitudinal axis 62 of the optical device 60 is offset in parallel with the longitudinal axis of the shaft 12, thereby resulting, in all, in an eccentric rotation of the shaft 12 around the optical device 60. In the area of the stationary jaw part 16 which, as well as the jaw part 17, is provided with an elongate transverse opening 96 and 97, respectively, the optical device 60 fits snugly into a radially outwardly pointing concave recess 98 of the stationary jaw part 16. The optical device 60 is thus guided on a side of the stationary jaw part 16 facing away from the movable jaw part 17. Damage to the optical device 60 by the two jaw parts 16 and 17 is thereby avoided.

The invention claimed is:

1. Endoscope comprising:
    a proximal end area,
    a distal end area introducible into the body of a human being,
    a shaft extending in a longitudinal direction,
    an optical device extending through the shaft in the longitudinal direction thereof and movable relative to the shaft, an inflow channel for feeding a fluid from the proximal end area to the distal end area, an outflow channel for conducting a fluid away from the distal end area to the proximal end area, an inflow connection in flow communication with the inflow channel, and an outflow connection in flow communication with the outflow channel, wherein:

the optical device is fixable in an axial direction relative to the shaft in a first precisely defined position and in at least a second precisely defined position differing from the first position at least with regard to the longitudinal direction, the inflow connection, the outflow connection and the optical device are rotatable relative to one another about an axis of rotation extending substantially in the longitudinal direction of the shaft; and in a third position, the optical device is fixable in the axial direction and freely rotatable about the axis of rotation.

2. Endoscope in accordance with claim 1, wherein at least one locking device is provided for fixing the optical device in at least one of the first position and the second position.

3. Endoscope in accordance with claim 1, wherein in at least one of the first position and the second position, the optical device is fixed in a circumferential direction relative to the shaft.

4. Endoscope in accordance with claim 1, wherein in the first position, a distal end of the optical device projects over the distal end of the endoscope.

5. Endoscope in accordance with claim 1, wherein in the second position, a distal end of the optical device projects over a distal end of the shaft, and the distal end area of the endoscope projects over the optical device.

6. Endoscope in accordance with claim 1, wherein the endoscope further comprises a device for receiving the optical device, and the device for receiving the optical device is movable relative to the shaft and fixable in the axial direction in at least one of the first position, the second position, and the third position.

7. Endoscope in accordance with claim 6, wherein the optical device is freely rotatable about a longitudinal axis of the optical device relative to the device for receiving the optical device.

8. Endoscope in accordance with claim 2, wherein the locking device comprises a locking member movable relative to a locking recess, one of the locking recess or the locking member is arranged on the optical device or on a device for receiving the optical device, and the other of the locking member or the locking recess is arranged on a receptacle of the endoscope for the optical device or for the device for receiving the optical device.

9. Endoscope in accordance with claim 1, wherein at least one movable tool is arranged at the distal end of the shaft.

10. Endoscope in accordance with claim 9, wherein the movable tool is rotatable relative to the shaft about the axis of rotation extending substantially in the longitudinal direction of the shaft.

11. Endoscope in accordance with claim 9, wherein the tool comprises at least one jaw part which is mounted for movement relative to the shaft.

12. Endoscope in accordance with claim 11, wherein at least two jaw parts movable relative to each other are provided.

13. Endoscope in accordance with claim 11, wherein at least one movable jaw part is pivotable relative to the shaft about a pivot axis extending substantially transversely to the longitudinal direction of the shaft.

14. Endoscope in accordance with claim 11, wherein an actuating device associated with the at least one jaw part is provided, and the actuating device is rotatable relative to the shaft.

15. Endoscope in accordance with claim 14, wherein the actuating device is lockable in an actuated position of the at least one movable jaw part.

16. Endoscope in accordance with claim 11, wherein at least two jaw parts are provided, which, in a closed position in which the two jaw parts rest against each other, are formed symmetrically in relation to a plane containing a longitudinal axis of the shaft.

17. Endoscope in accordance with claim 1, wherein the shaft has adjacent to the distal end of the endoscope a shaft section which is introducible into the body of a human being, an axis of symmetry of the optical device extends in the area of the shaft section parallel to an axis of symmetry of the shaft in an area of the shaft section, and the two axes of symmetry are spaced from each other.

18. Endoscope in accordance with claim 1, wherein an HF connecting device is provided for connecting the endoscope to a high-frequency generator, and the HF connecting device is arranged for rotation relative to the optical device.

19. Endoscope comprising:

a proximal end area, a distal end area introducible into the body of a human being, a shaft extending in a longitudinal direction, an optical device extending through the shaft in the longitudinal direction thereof and movable relative to the shaft, an inflow channel for feeding a fluid from the proximal end area to the distal end area, an outflow channel for conducting a fluid away from the distal end area to the proximal end area, an inflow connection in flow communication with the inflow channel, and an outflow connection in flow communication with the outflow channel, wherein:

the optical device is fixable in an axial direction relative to the shaft in a first precisely defined position and in at least a second precisely defined position differing from the first position at least with regard to the longitudinal direction, and the inflow connection, the outflow connection and the optical device are rotatable relative to the shaft about an axis of rotation extending substantially in the longitudinal direction of the shaft; and in a third position, the optical device is fixable in the axial direction and freely rotatable about the axis of rotation.

20. Endoscope in accordance with claim 19, wherein an HF connecting device is provided for connecting the endoscope to a high-frequency generator, and the HF connecting device is arranged for rotation relative to the optical device.

21. Endoscope comprising:

a proximal end area, a distal end area introducible into the body of a human being, a shaft extending in a longitudinal direction, an optical device extending through the shaft in the longitudinal direction thereof and movable relative to the shaft, and at least one movable tool arranged at the distal end of the shaft, wherein:

the optical device is fixable in an axial direction relative to the shaft in a first precisely defined position and in at least a second precisely defined position differing from the first position at least with regard to the longitudinal direction, the tool comprises at least two jaw parts, at least one of the at least two jaw parts being mounted for movement relative to the shaft, the at least two jaw parts, in a closed position in which the at least two jaw parts rest against each other, are formed symmetrically in relation to a plane containing a longitudinal axis of the shaft, and the optical device is arranged in an area of the at least two jaw parts on a first side of a stationary jaw part, and the movable jaw part is arranged at a second side of the stationary jaw part which faces away from the optical device.

22. Endoscope in accordance with claim 21, wherein in a third position, the optical device is fixable in the axial direction and freely rotatable about the longitudinal axis of the shaft.

23. Endoscope in accordance with claim 21, wherein the endoscope further comprises:

an inflow channel for feeding a fluid from the proximal end area to the distal end area, an outflow channel for conducting a fluid away from the distal end area to the proximal end area, an inflow connection in flow communication with the inflow channel, and an outflow connection in flow communication with the outflow channel.

24. Endoscope in accordance with claim 23, wherein the inflow connection, the outflow connection and the optical device are rotatable relative to one another about an axis of rotation extending substantially in the longitudinal direction of the shaft.

25. Endoscope in accordance with claim 21, wherein the stationary jaw part is of a concavely curved configuration in a direction pointing towards the optical device.

26. Endoscope in accordance with claim 21, wherein an HF connecting device is provided for connecting the endoscope to a high-frequency generator, and the HF connecting device is arranged for rotation relative to the optical device.

27. Endoscope comprising:

a proximal end area, a distal end area introducible into the body of a human being, a shaft extending in a longitudinal direction, and an optical device extending through the shaft in the longitudinal direction thereof and movable relative to the shaft, wherein:

the optical device is fixable in an axial direction relative to the shaft in a first precisely defined position and in at least a second precisely defined position differing from the first position at least with regard to the longitudinal direction, in a third position, the optical device is fixable in the axial direction and freely rotatable about a longitudinal axis of the shaft; and an HF connecting device is provided for connecting the endoscope to a high-frequency generator, and the HF connecting device is arranged for rotation relative to the optical device.

* * * * *

UNITED STATES PATENT AND TRADEMARK OFFICE
CERTIFICATE OF CORRECTION

PATENT NO.        : 7,615,002 B2                                           Page 1 of 1
APPLICATION NO.   : 10/886058
DATED             : November 10, 2009
INVENTOR(S)       : Rothweiler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1526 days.

Signed and Sealed this

Nineteenth Day of October, 2010

David J. Kappos
*Director of the United States Patent and Trademark Office*